United States Patent [19]

Schaar

[11] 3,990,450
[45] *Nov. 9, 1976

[54] DIAPER WITH ELASTIC WAIST MEANS

[75] Inventor: Charles H. Schaar, Lake Zurich, Ill.

[73] Assignee: Colgate-Palmolive Company, New York, N.Y.

[ * ] Notice: The portion of the term of this patent subsequent to Apr. 20, 1993, has been disclaimed.

[22] Filed: Dec. 22, 1975

[21] Appl. No.: 643,288

Related U.S. Application Data

[62] Division of Ser. No. 519,493, Oct. 31, 1974, Pat. No. 3,951,150.

[52] U.S. Cl. .............................. 128/287; 128/284
[51] Int. Cl.² ................... A61F 13/16; A41B 13/02
[58] Field of Search ................ 128/284, 287, 290 R, 128/296

[56] References Cited
UNITED STATES PATENTS

| | | | |
|---|---|---|---|
| 2,834,347 | 5/1968 | Connally | 128/284 |
| 3,530,859 | 9/1970 | Heimowitz | 128/284 |
| 3,642,001 | 2/1972 | Sabee | 128/287 |
| 3,731,688 | 5/1973 | Litt | 128/287 |
| 3,750,669 | 8/1973 | De Luca | 128/287 |
| 3,776,232 | 12/1973 | Schaar | 128/287 |
| 3,800,796 | 4/1974 | Jacob | 128/284 |
| 3,920,018 | 11/1975 | Schaar | 128/287 |
| 3,951,150 | 4/1976 | Schaar | 128/287 |
| R26,151 | 1/1967 | Duncan | 128/284 |

Primary Examiner—Aldrich F. Medbery
Attorney, Agent, or Firm—Powell L. Sprunger

[57] ABSTRACT

A disposable diaper comprising, an absorbent pad assembly having front and back waistline portions, and pleat means being laterally expandable in at least one waistline portion. The diaper has elastic means in the one waistline portion laterally constraining the one waistline portion when expanded to provide a snug fit of the diaper around the waistline of an infant.

20 Claims, 40 Drawing Figures

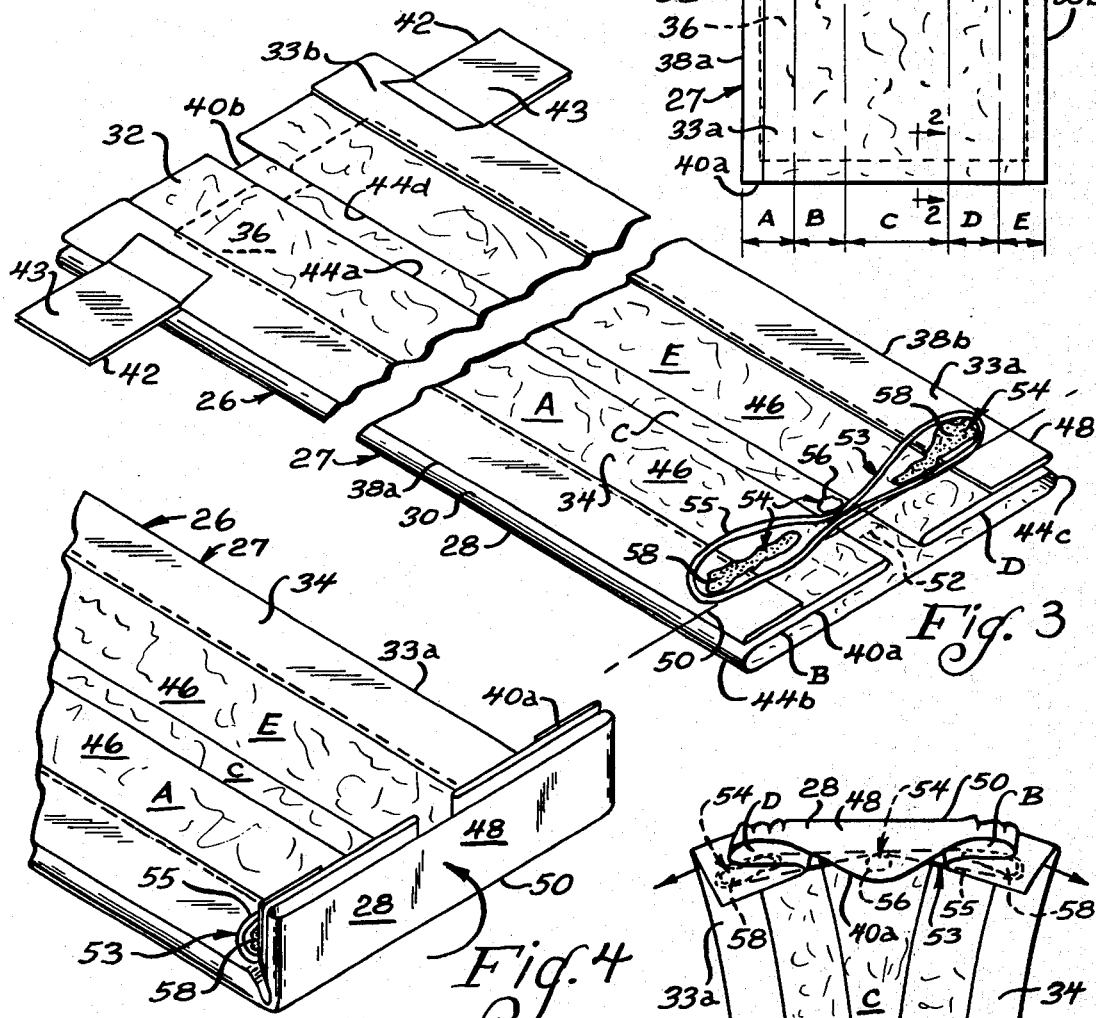

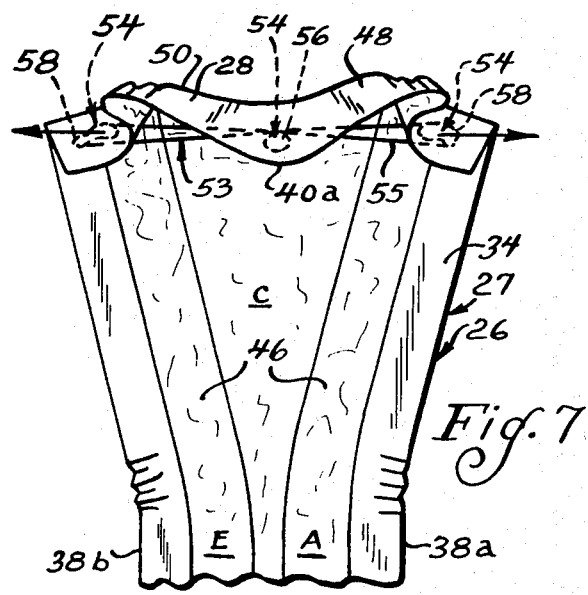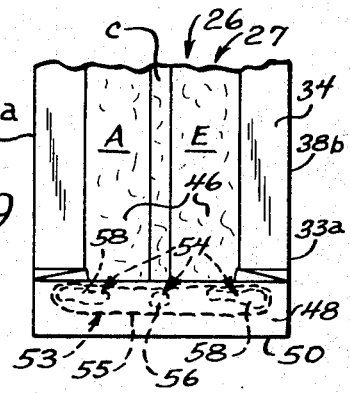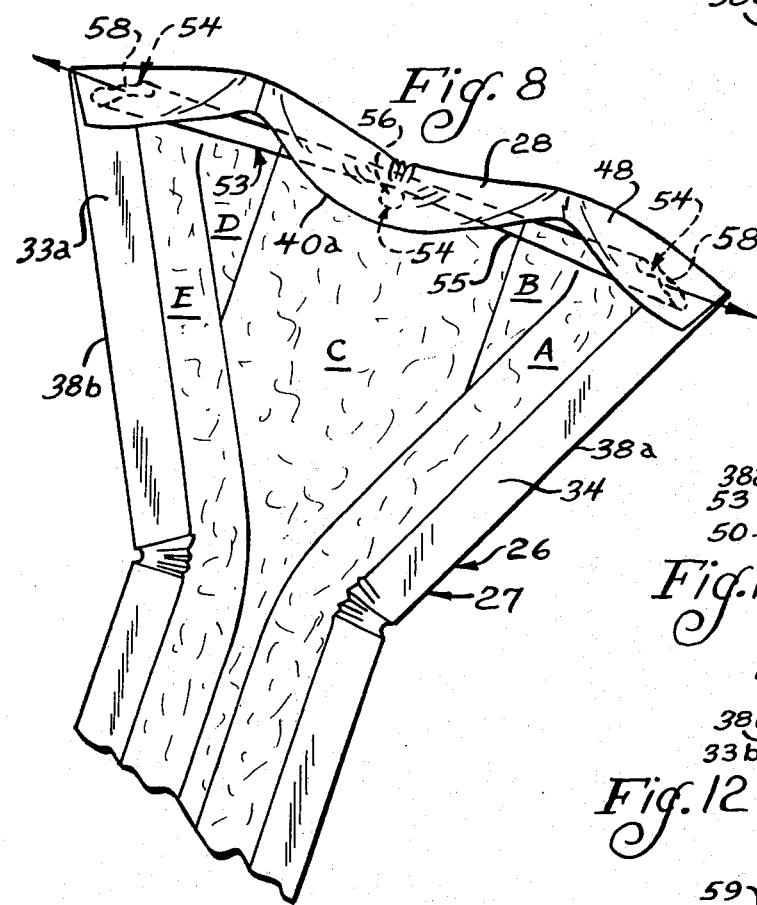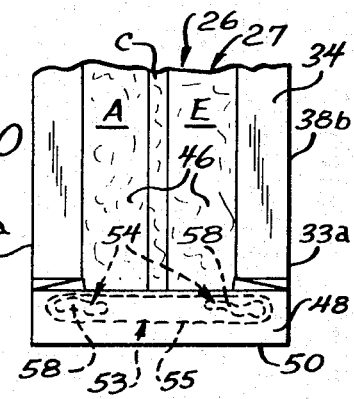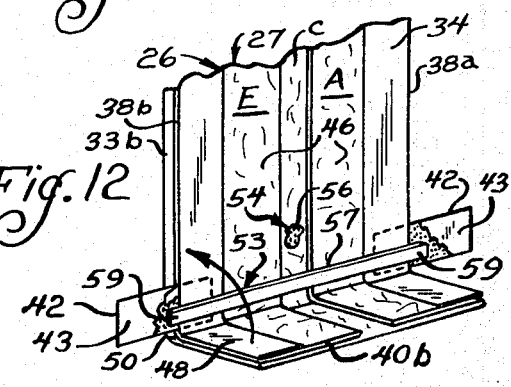

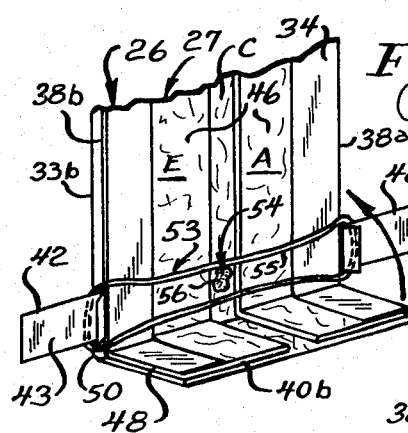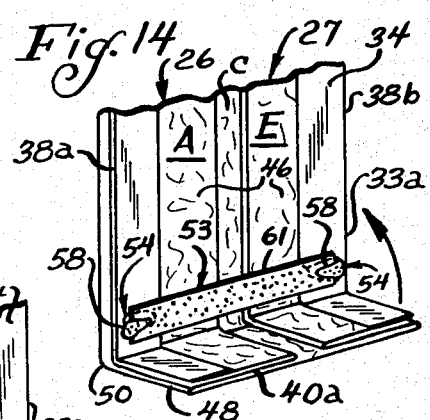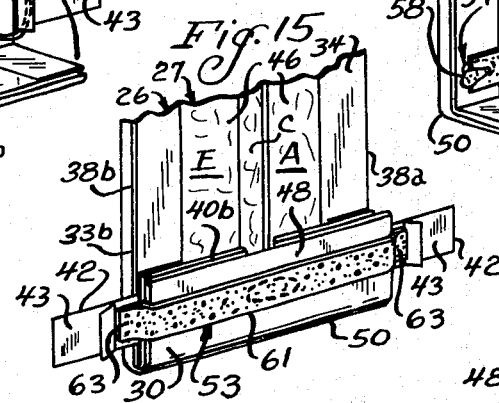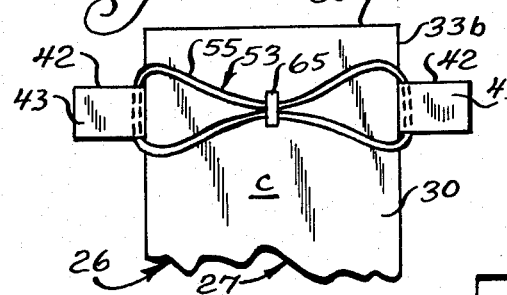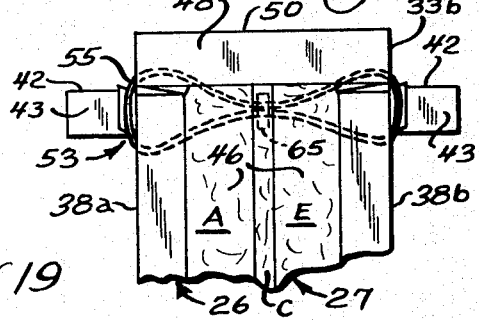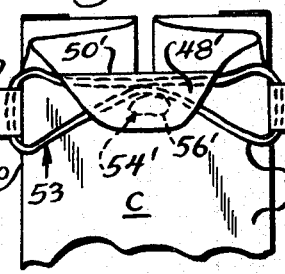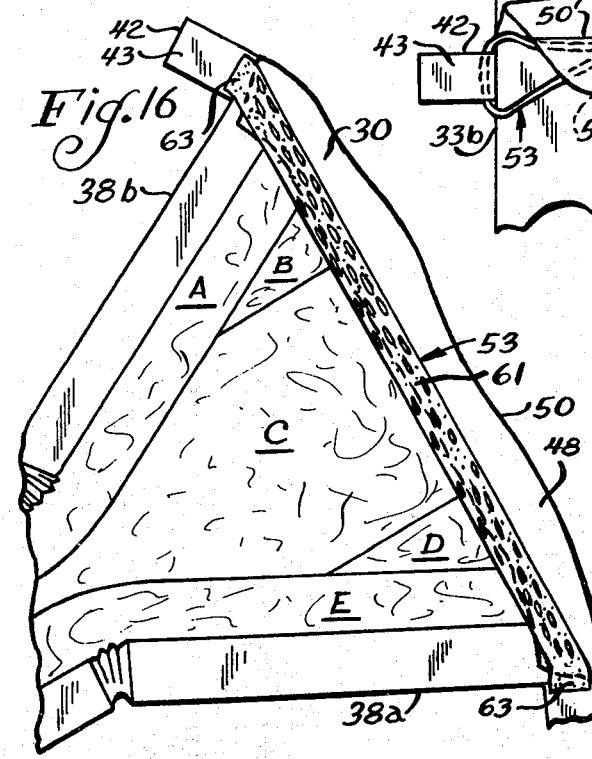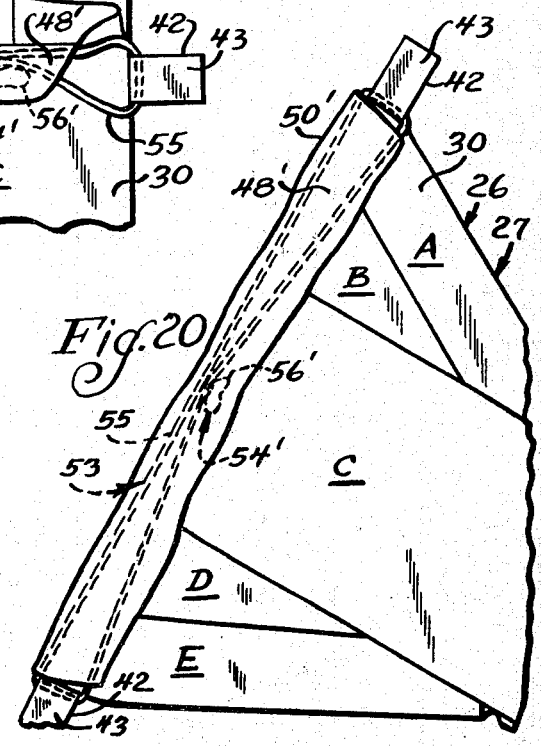

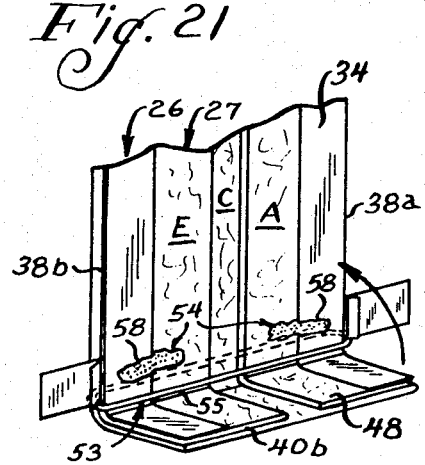
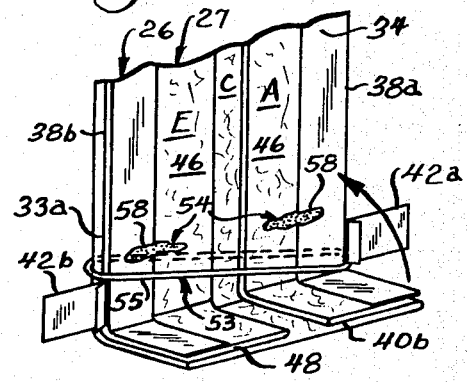
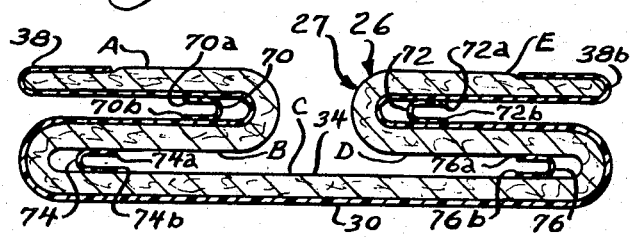
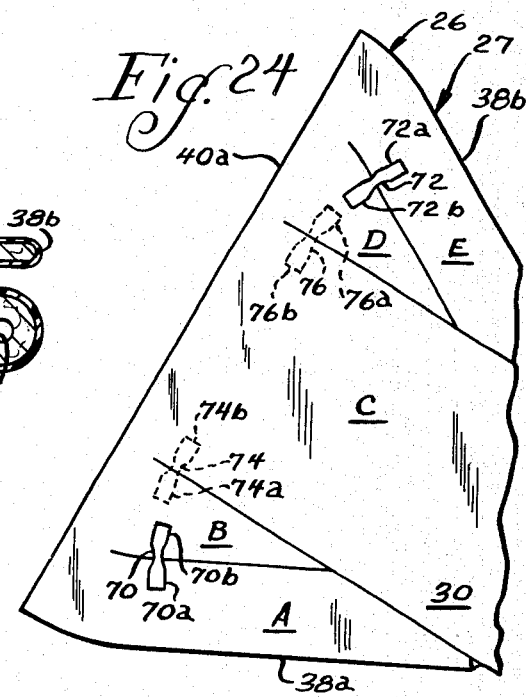
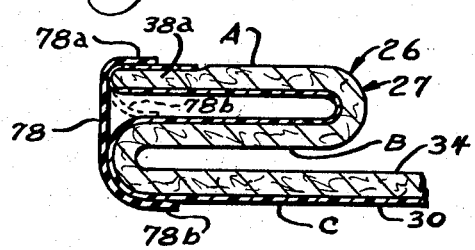
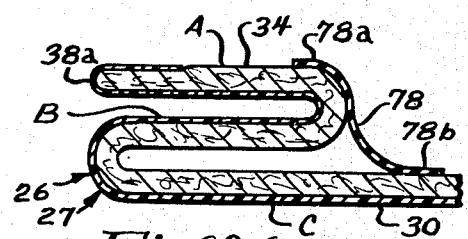

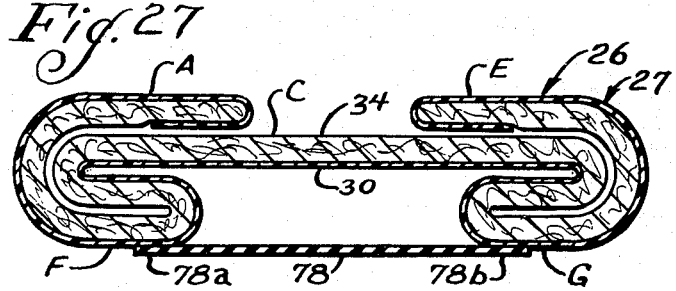
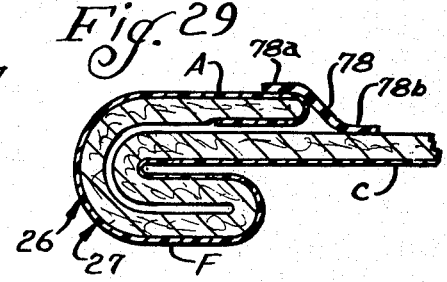
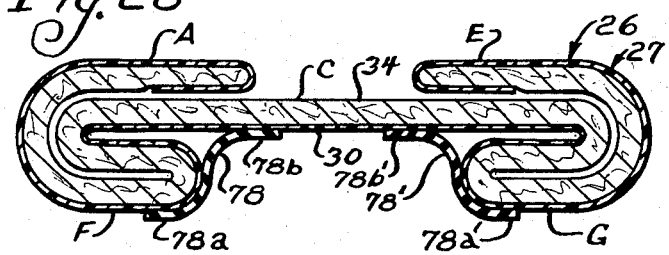
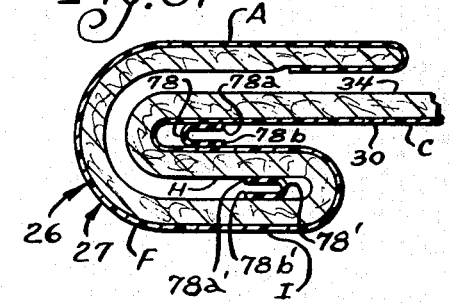
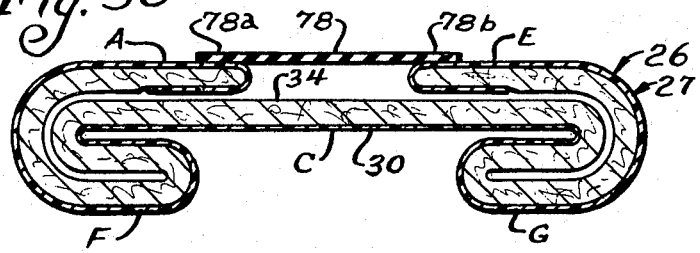
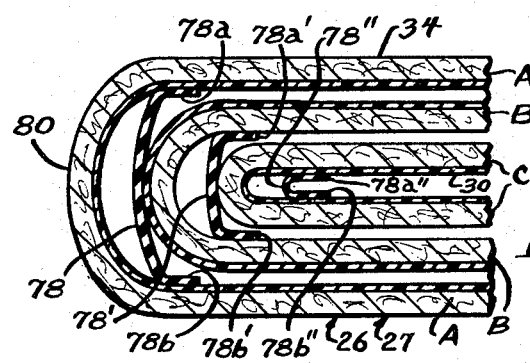
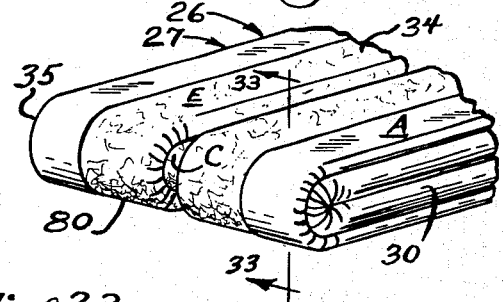
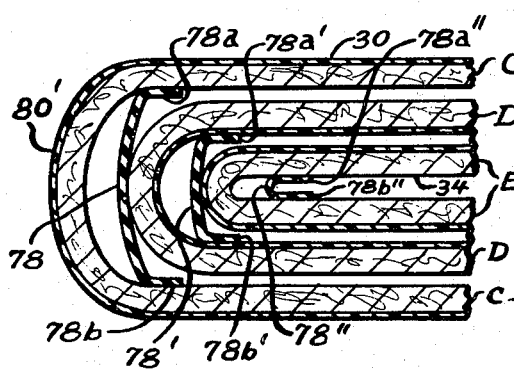
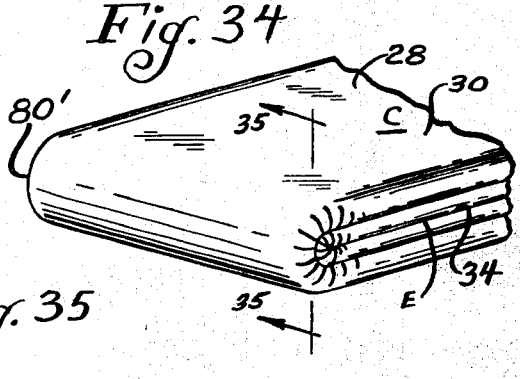

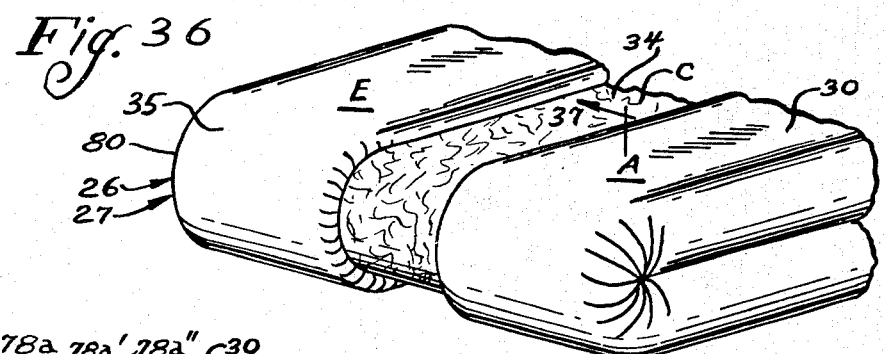
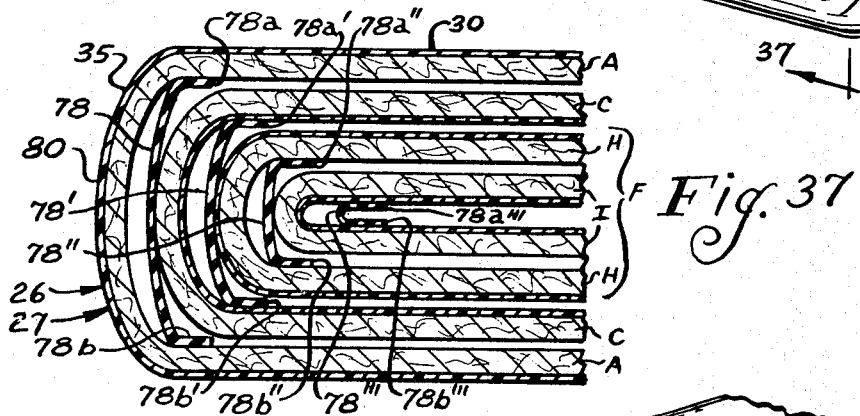
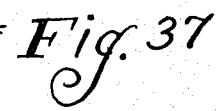
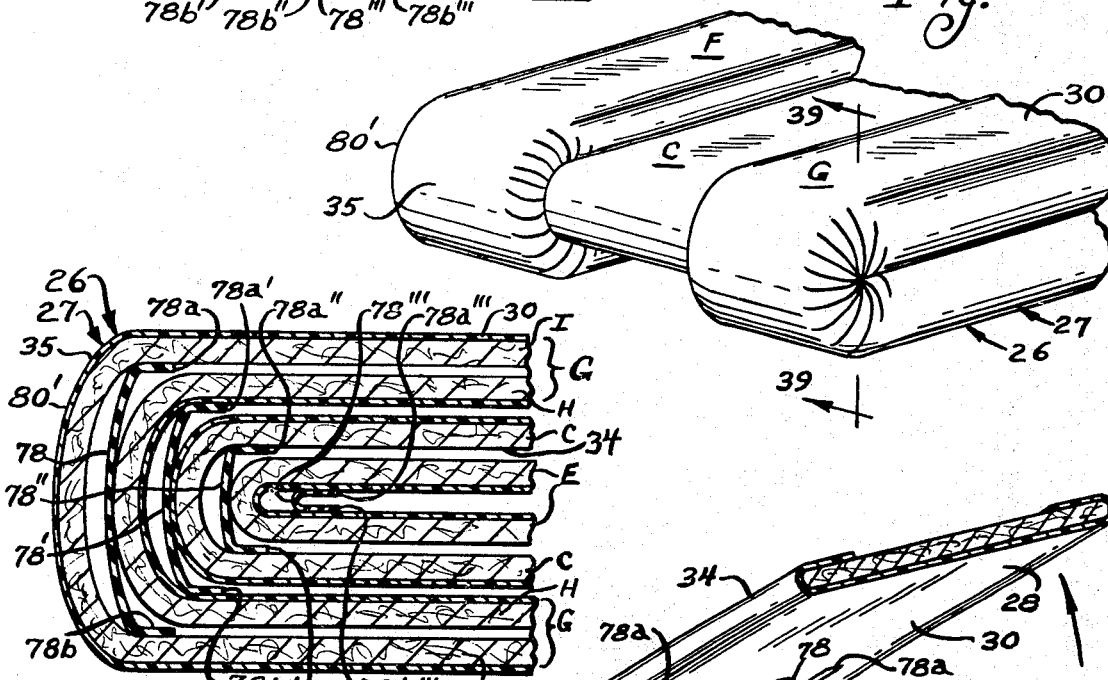
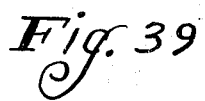
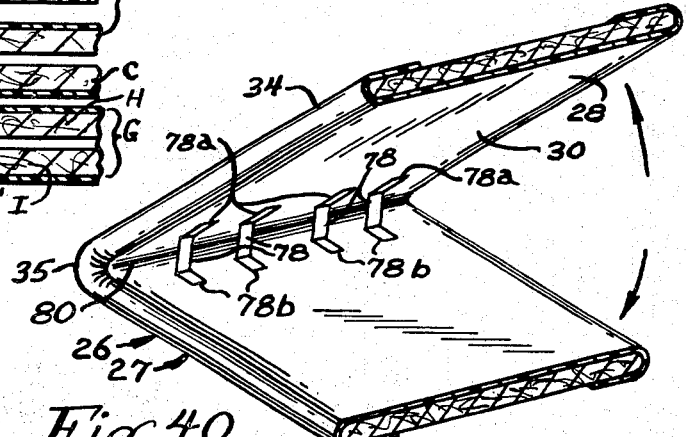
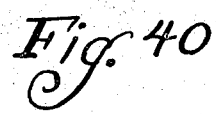

DIAPER WITH ELASTIC WAIST MEANS

This is a division of Sr. No. 519,493 filed Oct. 31, 1974, now U.S. Pat. No. 3,951,150.

BACKGROUND OF THE INVENTION

The present invention relates to absorbent articles, and more particularly to disposable diapers.

During recent years diapers of the disposable type have come into widespread use. Although disposable diapers have attained popularity with parents due to convenience, unfavorable comments have been made about leakage from the diapers during use and their fit on the infant. In particular, the ends of the diaper are normally susceptible to leakage due, in part, to a loose fit of the diaper about the infant.

Many of the present disposable diapers have tape strips located adjacent one end of the diapers. The diapers are normally placed on the infant by laying the infant on the diaper with the strip bearing part of the diaper being located beneath the back waistline of the infant. After removal of release sheets from the tape strips, attachment portions of the strips are brought around the infant's legs, and anchored to the front portion of the diaper. However, in order to obtain a tight fit of the diaper and prevent leakage about the infant's legs, the attachment portions of the strips are frequently secured at a location on the front portion of the diaper which is spaced somewhat from the front end edge or waistline of the diaper.

Since the permanently anchored portions of the strips are usually located adjacent the back end edge of the diaper, after placement of the diaper the tape strips apply tension to the back waistline of the diaper and thus may maintain a relatively close fit of the diaper against the back waistline of the infant. In contrast, the attachment portions of the strips are often spaced from the front waistline of the diaper, and significant tension is not applied by the strips against the diaper front waistline. The front waistline of the diaper is thus permitted to gap away from the infant, increasing the possibility of urine leakage in this area of the diaper, in spite that the front waistline of the diaper is normally more susceptible to urine leakage than the back waistline, since it is closer to the site of urine deposition on the diaper. Also, infants are generally inclined to spend more time on their stomachs than their backs, causing gravity to drive urine in the diaper with greater frequency toward the front waistline. Thus, the diaper ends are normally susceptible to leakage where it should most be prevented.

SUMMARY OF THE INVENTION

A principle feature of the present invention is the provision of a disposable diaper of simplified construction which provides an improved fit and minimizes leakage at an end of the diaper.

The diaper of the present invention comprises, an absorbent pad assembly having front and back waistline portions, and pleat means laterally expandable in at least one waistline portion. The diaper has elastic means in the one waistline portion laterally constraining the one waistline portion when expanded.

Thus, a feature of the invention is that the constrained waistline portion provides a snug fit of the diaper around the waistline of the infant.

Another feature of the invention is that the constrained waistline portion reduces leakage from an end of the diaper.

A further feature of the invention is that the constrained waistline portion provides a comfortable fit of the diaper on the infant.

Still another feature of the invention is that the elastic means is actuated by lateral expansion of the pleat means to constrain the waistline portion.

Yet another feature of the invention is that in another embodiment of the diaper the elastic means longitudinally constrains the pad assembly in the crotch region to obtain a snug fit and prevent leakage.

Further features will become more fully apparent in the following description of the embodiments of this invention and from the appended claims.

DESCRIPTION OF THE DRAWINGS

In the drawings:

FIG. 1 is a front plan view of a flat disposable diaper;

FIG. 2 is a fragmentary sectional view taken substantially as indicated along the line 2—2 of FIG. 1.

FIG. 3 is a fragmentary perspective view of the diaper of FIG. 1 after having been folded into a box-pleat configuration, and illustrating elastic means in a waistline portion of the diaper according to the present invention;

FIG. 4 is a fragmentary perspective view illustrating the formation of a diaper of the present invention;

FIG. 5 is a fragmentary front plan view of an embodiment of a diaper of the present invention;

FIGS. 6–8 are fragmentary plan views illustrating configurations of the diaper of FIG. 5 as the diaper is unfolded for placement on an infant;

FIG. 9 is a fragmentary front plan view of another embodiment of the diaper of the present invention;

FIG. 10 is a fragmentary front plan view of another embodiment of the diaper of the present invention;

FIG. 11 is a fragmentary perspective view of a partially folded diaper in another embodiment of the diaper of the present invention;

FIG. 12 is a fragmentary perspective view of a partially folded diaper in another embodiment of the diaper of the present invention;

FIG. 13 is a fragmentary perspective view of a partially folded diaper in another embodiment of the diaper of the present invention;

FIG. 14 is a fragmentary perspective view of a partially folded diaper in another embodiment of the diaper of the present invention.

FIG. 5 is a fragmentary perspective view of another embodiment of the diaper of the present invention;

FIG. 16 is a fragmentary perspective view, taken from the front, of the diaper of FIG. 15 as unfolded preparatory to placement on an infant;

FIG. 17 is a fragmentary back plan view of another embodiment of the diaper of the present invention;

FIG. 18 is a fragmentary front plan view of the diaper of FIG. 17;

FIG. 19 is a fragmentary back plan view of another embodiment of the diaper of the present invention;

FIG. 20 is a fragmentary back plan view of the diaper of FIG. 19 as unfolded preparatory to placement on an infant;

FIG. 21 is a fragmentary perspective view of a partially folded diaper in another embodiment of the diaper of the present invention;

FIG. 22 is a fragmentary perspective view of a partially folded diaper in another embodiment of the diaper of the present invention;

FIG. 23 is a sectional view of another embodiment of a diaper of the present invention;

FIG. 24 is a fragmentary back plan view of the diaper of FIG. 23 after being laterally unfolded;

FIG. 25 is a fragmentary sectional view of another embodiment of the present invention;

FIG. 26 is a fragmentary sectional view of another embodiment of the present invention;

FIG. 27 is a sectional view of another embodiment of a diaper of the present invention.

FIG. 28 is a sectional view of another embodiment of a diaper of the present invention;

FIG. 29 is a fragmentary sectional view of another embodiment of the present invention;

FIG. 30 is a sectional view of another embodiment of a diaper of the present invention;

FIG. 31 is a fragmentary sectional view of another embodiment of the present invention;

FIG. 32 is a fragmentary perspective view of another embodiment of the diaper of the present invention;

FIG. 33 is a fragmentary sectional view taken substantially as indicated along the line 33—33 of FIG. 32;

FIG. 34 is a fragmentary perspective view of another embodiment of the diaper of the present invention;

FIG. 35 is a fragmentary sectional view taken substantially as indicated along the line 35—35 of FIG. 34;

FIG. 36 is a fragmentary perspective view of another embodiment of the diaper of the present invention;

FIG. 37 is a fragmentary sectional view taken substantially as indicated along the line 37—37 of FIG. 36;

FIG. 38 is a fragmentary perspective view of another embodiment of the diaper of the present invention;

FIG. 39 is a fragmentary sectional view taken substantially as indicated along the line 39—39 of FIG. 38; and FIG. 40 is a fragmentary perspective view of another embodiment of the diaper of the present invention;

DESCRIPTION OF THE PREFERRED EMBODIMENTS

Referring now to FIGS. 1 and 2, there is shown a flat diaper designated generally 26 having an absorbent pad assembly 27. The pad assembly 27 has a fluid impervious backing sheet 28 defining a back surface 30 of the pad assembly, a fluid pervious cover or top sheet 32 defining a substantial portion of a front surface 34 of the pad assembly, an absorbent pad 36 positioned intermediate the backing sheet 28 and cover sheet 32, front and back waistline portions 33a and 33b, and a crotch portion 35 intermediate the waistline portions 33a and b. The diaper or pad assembly has a pair of side edges 38a and 38b, and a pair of end edges 40a and 40b connecting the side edges 38a and b. The diaper 26 may also have a pair of conventional tape fasteners 42 adjacent one end edge 40b of the diaper for securing the diaper about an infant during placement, with securing portions 43 of the fasteners 42 extending past the side edges 38a and b of the pad assembly. As best shown in FIG. 2, the top and backing sheets 32 and 28, respectively, may extend to the end edges of the diaper.

The flat diaper 26 of FIG. 1 has a plurality of longitudinally extending folds about fold lines 44a, 44b, 44c, and 44d, defining a box-pleat configuration of the diaper, as shown in FIG. 3. As illustrated in FIGS. 1 and 3, the box-pleat diaper 26 has a longitudinally extending central panel C, a pair of first panels B and D extending from and overlying the central panel C, and a pair of outermost panels A and E extending from and overlying the first panels B and D. The pleat means 46 of the box-pleat diaper may be spaced apart in a lateral central portion of the diaper, as shown in FIG. 3, for a purpose which will be described below. As is apparent, the outermost panels A and E may be moved laterally in the waistline portions 33a and b of the pad assembly to laterally expand the pleat means.

As is illustrated in FIGS. 2–4, the box-pleat diaper 26 has an end section or flap 48 adjacent the end edge 40a, which may be folded about a lateral fold line 50 over the front surface 34 of the diaper, such that the front surface 34 of the end section or flap means 48 engages against the front surface 34 of the diaper adjacent the end section 48. Preferably, the end edge 52 of the absorbent pad 36 most adjacent the end edge 40a of the diaper is spaced from the end edge 40a, and the fold line 50 of the end section 48 is located adjacent the end edge 52 of the absorbent pad 36, in order that the backing sheet 28 in the end section 48 overlies an end portion of the absorbent pad when the end section is folded into place on top of the diaper.

As illustrated in FIG. 3, the diaper 26 has laterally extending elastic band means 53 in the form of an elastic loop 55. The elastic loop 55 extends across front surface 34 of the outermost panels A and E adjacent the fold line 50. The diaper also has securing means 54, such as adhesive, to retain a portion of the front surface 34 of the end section 48 against the underlying front surface 34 of the box-pleat diaper. Although for convenience the securing means 54 is described in connection with the use of adhesive, it will be understood that other suitable securing means may be utilized to retain the front surface of the end section to the underlying front surface of the diaper, such as by heat sealing.

In this embodiment, the securing means 54 comprises a spot of adhesive 56 intermediate the spaced pleat means 46 on the front surface 34 of the central panel C adjacent the fold line 50, and a pair of adhesive lines or spots 58 on the front surface of the outermost panels A and E adjacent the fold line 50. The adhesive spot 56 retains the front surface 34 of the central panel C in the end section 48 against the underlying front surface 34 of the central panel C of the diaper. Similarly, the adhesive lines 58 retain the front surface 34 of the outermost panels A and E in the end section 48 against the front surface 34 of the underlying portions of the outermost panels in the diaper.

As shown, the elastic loop 55 passes around the adhesive lines or spots 58, and courses of the loop 55 are located intermediate the adhesive spot 56 and the fold line 50. After the end section 48 has been folded over the top of the diaper, as shown in FIG. 4, the end section 48 may be pressed against the underlying portion of the diaper to obtain a good set of the adhesive and retain the end section 48 in place. Thus, as shown in FIG. 5, when the end section 48 is attached to the underlying front surface of the diaper, the elastic loop 55 is captured beneath the end section 48 by the adhesive lines 58. Although, for convenience, the elastic means 53 and end section 48 are described in connection with the front waistline portion 33a, it is apparent that a similar structure may be included in the back waistline portion 33b, or both waistline portions, if desired, in this and many of the other embodiments of the present invention.

The use of the elastic band means 53 in conjunction with the folded oven end section 48 to provide a snug fit of the diaper and minimize leakage is described in connection with FIGS. 6-8. As the end of the box-pleat diaper 26 adjacent the end section 48 is unfolded during placement of the diaper on an infant, the spots of adhesive 56 and 58 or securing means 54 maintain front surface portions of the end section 48 against the underlying front surface 34 of the diaper, and retain the elastic loop 55 in place beneath the end section 48. Thus, as shown in FIGS. 6 and 7, as the outermost panels A and E of the diaper are spread outwardly, the outermost panels of the end section 48 are unfolded from under the central panel C of the end section, and the captured elastic loop 55 is expanded by the adhesive lines 58. When the end of the diaper is completely unfolded, as shown in FIG. 8, the securing means 54 retains the entire length of the end section 48 in an overlying relationship with the portion of the diaper adjacent the end section 48. In this configuration, the adhesive spot 56 retains the central panel C of the end section 48 against the underlying portion of the diaper central panel, while the adhesive lines 58 retain the outermost panels of the end section 48 against the underlying outermost panels of the pad assembly or diaper. Additionally, the captured elastic loop 55 is expanded and actuated responsive to lateral expansion of the pleat means, and causes a gathering of the pad assembly in the waistline portion 33a. Thus, the elastic loop laterally constrains the waistline portion of the pad assembly, and when the diaper is placed on an infant after securement by the tape fasteners the waistline portion is brought into close contact by the elastic loop to obtain a snug fit about the waistline of the infant. As shown, the end section 48 substantially covers the elastic band means 53 to prevent contact of the band means against the skin of the infant.

Accordingly, when the box-pleat diaper is completely unfolded, the folded over portion of the fluid impervious backing sheet 28 serves to form a waterproof sealing barrier to prevent leakage at the end of the diaper. Since the folded over backing sheet in the end section preferably overlies an end portion of the absorbent pad, the backing sheet forms a waterproof pocket to capture urine which may wick from the end edge of the absorbent pad, and thus prevents leakage. It is noted that the securing means 54 of the unfolded diaper of FIG. 8 retains only spaced areas of the end section against the diaper. Thus, the regions of the backing sheet in the end section 48 intermediate the adhesive spots 56 and 58 are permitted to gap away from the underlying front surface of the diaper. The elastic band means 53 brings the waistline portion of the diaper into close contact with the infant's skin, and these free regions of the end section serve to form a gasket against the infant's skin and aid in preventing leakage of urine from the diaper. Additionally, the elastic means assists in retaining the diaper about the infant, and permits the use of tape fasteners of reduced strength, thus reducing the cost of the fasteners and diaper to the consumer.

Another embodiment of the diaper of the present invention is illustrated in FIG. 9, in which like reference numerals designate like parts. In this embodiment, the courses of the elastic loop 55 pass on opposite sides of the adhesive spot 56. In other respects the diaper of FIG. 9 is similar to the diaper described in connection with FIGS. 1-8, and operates similarly to obtain a close fit of the waistline portion about the infant.

Another embodiment of the present invention is illustrated in FIG. 10, in which like reference numerals designate like parts. In this embodiment, which is similar in most respects to the diapers previously described, the adhesive spot 56 is omitted from the pad assembly, and the adhesive lines or spots 58 of the securing means 54 retain the elastic loop 55 beneath the end section 48, as previously described, and retain the end section 48 in its overlying relationship when the diaper is expanded.

Another embodiment of the diaper of the present invention is illustrated in FIG. 11, in which like reference numerals designate like parts. In this embodiment, the elastic means 53 comprises an elastic strip 57 which is secured to the front surface 34 of the outermost panels A and E. The strip 57 may comprise a pressure-sensitive tape having an elastic backing and adhesive adjacent its end secured to the outermost panels. The end section 48 may be retained in place over the strip 57 by securing means 54. The elastic strip 57 operates similar to the elastic loop 53 to obtain a close fit of the waistline portion of the diaper, as previously described.

Another embodiment of the diaper of the present invention is illustrated in FIG. 12, in which like reference numerals designate like parts. In this embodiment, the elastic strip 57 has end portions 59 which are secured to adhesive on the securing portions 43 of the tape fasteners 42, in order to retain the elastic strip 57 in place over the front surface 34 of the outermost panels A and E. The end section 48 may be retained in place by securing means 54. When the outermost panels are moved laterally to expand the pleat means 46 during placement of the diaper, the adhesive on the tape fasteners retains the end portions 59 of the elastic strip 57, such that the strip 57 is expanded.

Another embodiment of the diaper of the present invention is illustrated in FIG. 13 in which like reference numerals designate like parts. In this embodiment, the elastic loop 55 extends around the securing portions 43 of the tape fasteners 42, and the tape fasteners retain the elastic loop in its proper position when the pleat means in the diaper is expanded for placement of the diaper on the infant. The end section 48 may be retained in place by securing means 54, as previously described.

Another embodiment of the diaper of the present invention is illustrated in FIG. 14, in which like reference numerals designate like parts. In this embodiment, the elastic band means 53 comprise a strip of elastic foam 61 having ends secured to the front surface 34 of the outermost panels A and E by securing means 54 which may also retain the end section 48 in place on the diaper.

Another embodiment of the diaper of the present invention is illustrated in FIGS. 15 and 16, in which like reference numerals designate like parts. In this embodiment, the elastic foam strip 61 has end portions 63 retained by the adhesive on the securing portions 43 of the tape fasteners 42, and the strip 61 passes over the back surface 30 of the end section 48. When the waistline portion of the pad assembly is laterally expanded, as shown in FIG. 16, the foam strip 61 covers a substantial portion of the folded over end section 48, and provides a particularly soft surface over the end section for the infant's skin.

Another embodiment of the diaper of the present invention is illustrated in FIGS. 17 and 18, in which like reference numerals designate like parts. In this embodiment, the elastic loop 55 extends around the securing portions 43 of the tape fasteners 42 and passes around the back surface 30 of the central panel C in the pad assembly. An intermediate portion of the elastic loop 55 may be secured to the back surface 30 of the central panel C by suitable means, such as a tape strip 65. The elastic loop 55 in the diaper of FIGS. 17 and 18 operates to laterally constrain the waistline portion of the diaper, as previously described, when the pleat means in the diaper is laterally expanded during placement of the diaper on the infant, with the securing portions 43 of the fasteners 42 retaining the loop in position in conjunction with the tape strip 65.

A somewhat similar embodiment of the diaper of the present invention is illustrated in FIGS. 19 and 20, in which like reference numerals designate like parts. In this embodiment, the elastic loop 55 also extends around the securing portions 43 of the tape fasteners 42 and the back surface 30 of the central panel C in the pad assembly. However, in this embodiment, the back surface of the central panel in an end section 48' is folded against the back surface 30 of the central panel C, as shown, and securing means 54', such as an adhesive spot 56', retains the central panel of the end section 48' against the back surface of the central panel C. The courses of the elastic loop 55 pass between the adhesive spot 56' and a fold line 50' defining the folded over end section 48'. When the pleat means in the diaper is laterally expanded, as shown in FIG. 20, the entire end section 48', including the first panels B and D and outermost panels A and E, as well as the central panel C, is folded over the back surface 30 of the diaper and covers a substantial portion of the elastic loop 55. The elastic loop 55 operates to laterally constrain the laterally expanded diaper and provide a good fit of the diaper around the waistline of an infant, as previously described.

Another embodiment of the diaper of the present invention is illustrated in FIG. 21, in which like reference numerals designate like parts. In this embodiment, the elastic loop 55 extends completely around the outer surface of the pleated diaper, and operates as previously described to laterally constrain the diaper when it is unfolded. The loop 55 may be retained in place by the end section 48 which is secured to the underlying front surface of the diaper by the securing means 54. Alternatively, or in combination with the end section 48, the tape fastener 42 may be utilized to prevent slippage of the loop 55 toward the crotch region of the diaper, thus retaining the loop at its desired location.

Another embodiment of the diaper of the present invention is illustrated in FIG. 22, in which like reference numerals designate like parts. In this embodiment, the elastic loop 55 extends around the outer surface of the pleated diaper, with the loop passing around the side edge 38a intermediate one tape fastener 42a and the end edge 40b, and passing around the other side edge 38b adjacent a side of the other tape fastener 42b remote the end edge 40b. It is apparent that the fasteners 42a and b alone will retain the loop 55 in place when the diaper is laterally unfolded, but the end section 48 may be folded over and secured to the underlying front surface of the diaper by securing means 54 in order to cover the loop, if desired.

Another embodiment of the diaper of the present invention is illustrated in FIGS. 23 and 24, in which like reference numerals designate like parts. As shown in FIG. 23, a plurality of elastic strips 70, 72, 74, and 76 have opposed ends 70a and 70b, 72a and 72b, 74a and 74b, and 76a and 76b, respectively, secured to exposed surfaces of adjacent panels in the pad assembly, such that the distance along the surfaces of the adjacent panels intermediate the opposed ends of each strip is preferably greater than the length between the opposed ends in each strip itself. Alternatively, the central portion of the strip may be placed under tension prior to unfolding the diaper. As illustrated in FIG. 24, when the diaper is laterally unfolded, the central portions of the strips assume a position adjacent the surface of the diaper under tension, and the strips thus laterally constrain the diaper. The strips 70 and 72 are shown as extending between the back surface 30 of the outermost panels A and E and the back surface 30 of the first panels B and D, respectively, while the strips 74 and 76 are shown as extending between the front surface 34 of the first panels B and D and the front surface 34 of the central panel C. It will be understood that the pad assembly 27 may have any suitable arrangement of the strips, such as the strips 70 and 72 or the strips 74 and 76 alone, and that the strips may be located at any desired longitudinal position in the diaper to produce the desired effect when the pad assembly is unfolded.

Thus, in FIG. 25, the box-pleat diaper has an elastic strip 78 having opposed ends 78a and b secured to the front surface 34 of the outermost panel A and the back surface 30 of the central panel C, as shown in solid lines, or the end 78b may be secured to the back surface 30 of the first panel B, as shown in dotted lines, with the central portion of the strip extending between the ends 78a and b. In FIG. 26, the strip 78 has its ends 78a and b secured to the front surface 34 of the outermost panel A and the front surface 34 of the central panel C, and may be used in lieu of the adhesive spots used to retain the pleats in place over the central panel, if desired.

The elastic strips may be utilized to laterally constrain an inverted pleat diaper, as described in connection with FIGS. 27–31 below. As shown in FIG. 27, the inverted pleat diaper 26 has a longitudinally extending central panel C, a pair of doubled back panels F and G extending from and underlying the back surface of the central panel C, and a pair of outermost panels A and E extending from the back panels F and G and overlying the front surface of the central panel C. The elastic strip 78 has its opposed ends 78a and b secured to the back surface 30 of the back panels F and G, such that the strip 78 laterally constrains the pad assembly when the diaper is unfolded.

The inverted pleat diaper of FIG. 28 includes a pair of elastic strips 78 and 78' having opposed ends 78a and b and 78a and b', respectively, secured to the back surface 30 of the back panels F and G and the back surface 30 of the central panel C. In FIG. 29, the opposed ends 78a and b of the elastic strip 78 are secured to the back surface 30 of the outermost panel A and the front surface 34 of the central panel C. As shown in FIG. 30, the elastic strip 78 may have its ends 78a and b secured to the back surface 30 of the outermost panels A and E. As illustrated in FIG. 31, the diaper 26 may include an elastic strip 78 having its ends 78a and b secured to the back surface 30 of the central panel C and the back surface 30 of a first section H in the back panel F, and/or an elastic strip 78' having its ends 78a' and 78b' secured to the front surfaces 34 of contiguous first and second sections H and I in the back panel F. In each case, the elastic strips are under tension, such as by expanding the strips from a relaxed state, when the pad assembly is unfolded to laterally constrain the diaper. As previously discussed, the elastic strips may be under some initial tension prior to unfolding the diaper, if desired.

The elastic strips or means may also be utilized to longitudinally constrain the diaper when it is unfolded, particularly in the crotch region of the diaper. A box pleat diaper is shown in FIGS. 32 and 33 which is folded for packaging along a lateral fold line 80 in the crotch region 35 such that the front surfaces of the central panel C and the outermost panels A and E face outwardly, and the back surfaces of contiguous longitudinal sections of the central panel C face each other. As shown in FIG. 33, the pad assembly 27 may have one or more elastic strips 78, 78', and 78'' on both sides of the diaper in the crotch region 35. Strips 78 have their opposed ends 78a and b secured to the back surfaces 30 of the outermost panels A and E on opposite sides of the fold line 80. Similarly, strips 78' have their ends 78' and 78b' secured to the front surfaces 34 of the first panels B and D, and strips 78'' have their ends 78a'' and 78b'' secured to the back surfaces 30 of the central panel on opposite sides of the fold line. When the diaper is unfolded about the fold line 80 during placement of the diaper, the strips are under tension, such as by expanding the strips, to longitudinally constrain the diaper in the crotch region, thus obtaining a snug fit of the diaper and preventing leakage. If the distance along the surface of the pad assembly between the opposed ends of the strips is greater than the length of the strips between their ends, the strips may be in a relaxed state prior to unfolding the diaper. Otherwise, the strips are secured to the diaper in a manner such that the strips are under tension prior to unfolding the diaper to achieve the desired effect when the diaper is unfolded.

In FIGS. 34 and 35 the box pleat diaper is shown folded along a lateral fold line 80' in the crotch region 35, with the back surface of the central panel C facing outwardly from the laterally folded diaper. As shown in FIG. 35, elastic strips 78 have their ends 78a and b secured to the front surface 34 of the central panel C on opposite sides of the fold line 80'. Similarly, strips 78' have their ends 78a' and 78b' secured to the back surfaces 30 of the first panels B and D, while strips 78'' have their ends 78a'' and 78b'' secured to the front surfaces 34 of the outermost panels A and E on opposite sides of the fold line 80'. It is apparent that in the above and following embodiments of the diaper, the elastic means may be located inside the panels themselves, if desired.

An inverted pleat diaper is shown in FIGS. 36 and 37 which is laterally folded along the fold line 80 in the crotch region 35 such that the back surface 30 of the outermost panels A and E and the front surface 34 of the central panel C face outwardly. The diaper includes one or more elastic strips 78, 78', 78'', and 78''' having their ends secured on opposite sides of the fold line 80. Strips 78 have their ends 78a and b secured to the front surface 34 of the outermost panels A and E, strips 78' have their ends 78a', and 78b' secured to the back surface 30 of the central panel C, strips 78'' have their ends 78a'' and 78b'' secured to the front surfaces 34 of the first sections H in the back panels F and G, and strips 78''' have their ends 78a''' and 78b''' secured to the back surfaces 30 of the second sections I in the back panels F and G. The inverted pleat diaper of FIGS. 38 and 39 is folded along the lateral fold line 80' in the crotch region 35 such that the back surface 30 of the back panels F and G and the central panel C face outwardly. One or more elastic strips 78, 78', 78'', and 78''' are secured on opposite sides of the fold line 80, as described below. Strips 78 have their ends 78a and b secured to the front surfaces 34 of the second sections I in the back panels F and G, strips 78' have their ends 78a' and 78b' secured to the back surfaces 30 of the first sections H in the back panels F and G, strips 78'' have their ends 78a'' and 78b'' secured to the front surface 34 of the central panel C, and the strips 78''' have their ends 78a''' and 78b''' secured to the back surfaces 30 of the outermost panels A and E. The elastic strips or means in the diapers of FIGS. 36–39 operate as previously described to longitudinally constrain the pad assembly in the crotch region when the diaper is longitudinally unfolded.

Another embodiment of the diaper of the present invention is illustrated in FIG. 40, in which like reference numerals designate like parts. In this embodiment, the flat diaper of FIG. 1 is folded in the crotch region 35 along a lateral fold line 80, such that the front surface 34 of the diaper faces outwardly. One or more elastic strips 78 have their opposed ends 78a and b secured to the back surface 30 of the diaper on opposite sides of the fold line 80. Thus, when the diaper is unfolded for placement of the diaper on an infant, as indicated by the direction of the arrows in the drawing, the strips 78 are under tension to longitudinally constrain the diaper in the crotch region, resulting in a snug fit of the diaper to provide comfort to the infant and prevent leakage.

The foregoing detailed description is given for clearness of understanding only and no unnecessary limitations should be understood therefrom, as modifications will be obvious to those skilled in the art.

I claim:

1. A disposable diaper, comprising: an absorbent pad assembly having an absorbent pad, a pair of waistline portions, a crotch portion intermediate said waistline portions, a front surface, a back surface, a pair of side edges, a pair of end edges connecting said side edges, a plurality of longitudinally extending folds defining a box-pleat configuration of the pad assembly, said pad assembly having a first pair of fold lines defining a longitudinally extending central panel, and a second pair of fold lines defining a pair of intermediate panels overlying the front surface of the central panel and a pair of outermost panels overlying the intermediate panels, and said pad assembly having an elastic band having a first end secured to said outermost panel and a second end secured to the back surface of the pad assembly adjacent said first fold line, said ends of the band being connected to the pad assembly at locations a similar distance from one edge of the pad assembly.

2. The diaper of claim 1 wherein said first end of the elastic band is secured to the front surface of the outermost panel.

3. The diaper of claim 1 wherein said second end of the elastic band is secured to the back surface of the central panel.

4. The diaper of claim 1 wherein said second end of the elastic band is secured to the back surface of said intermediate panel.

5. The diaper of claim 1 wherein said elastic band is located in one of said waistline portions of the pad assembly.

6. The diaper of claim 1 wherein said elastic band is located in said crotch portion of the pad assembly.

7. A disposable diaper, comprising: an absorbent pad assembly having an absorbent pad, a pair of waistline portions, a crotch portion intermediate said waistline portions, a front surface, a back surface, a pair of side edges, a pair of end edges connecting said side edges, a plurality of longitudinally extending folds defining a box-pleat configuration of the pad assembly, said pad assembly having a first pair of fold lines defining a longitudinally extending central panel, and a second pair of fold lines defining a pair of intermediate panels overlying the front surface of the central panel and a pair of outermost panels overlying the intermediate panels, and said pad assembly having an elastic band having a first end connected to the front surface of the central panel, and a second end connected to the front surface of the pad assembly adjacent said second fold line, said ends of the band being connected to the pad assembly at locations a similar distance from one edge of the pad assembly.

8. The diaper of claim 7 wherein said second end of the elastic band is connected to the front surface of the outermost panel of said pad assembly.

9. The diaper of claim 7 wherein said first end of the elastic band is connected to the central panel at a location intermediate said second fold lines.

10. The diaper of claim 7 wherein said elastic band is located in at least one of said waistline portions of the pad assembly.

11. The diaper of claim 7 wherein said elastic band is located in the crotch region of the pad assembly.

12. A disposable diaper, comprising: an absorbent pad assembly having an absorbent pad, a pair of waistline portions, a crotch portion intermediate said waistline portions, a front surface, a back surface, a pair of side edges, a pair of end edges connecting said side edges, a plurality of longitudinally extending folds defining a box-pleat configuration of the pad assembly, said pad assembly having a first pair of fold lines defining a longitudinally extending central panel, and a second pair of fold lines defining a pair of intermediate panels overlying the front surface of the central panel and a pair of outermost panels overlying the intermediate panels, and said pad assembly having an elastic band extending across said second fold line, said band having a first end secured to the back surface of the outermost panel, and a second end secured to the back surface of the intermediate panel, said ends of the band being connected to the pad assembly at locations a similar distance from one edge of the pad assembly.

13. The diaper of claim 12 wherein said band is located in at least one of the waistline portions of the pad assembly.

14. The diaper of claim 12 wherein said band is located in the crotch portion of the pad assembly.

15. A disposable diaper, comprising: an absorbent pad assembly having an absorbent pad, a pair of waistline portions, a crotch portion intermediate said waistline portions, a front surface, a back surface, a pair of side edges, a pair of end edges connecting said side edges, a plurality of longitudinally extending folds defining a box-pleat configuration of the pad assembly, said pad assembly having a first pair of fold lines defining a longitudinally extending central panel, and a second pair of fold lines defining a pair of intermediate panels overlying the front surface of the central panel and a pair of outermost panels overlying the intermediate panels, and said pad assembly having an elastic band extending across said first fold line, said band having a first end secured to the front surface of the intermediate panel, and a second end secured to the front surface of said central panel, said ends of the band being connected to the pad assembly at locations a similar distance from one edge of the pad assembly.

16. The diaper of claim 15 wherein said band is located in at least one of said waistline portions of the pad assembly.

17. The diaper of claim 15 wherein said band is located in said crotch portion of the pad assembly.

18. A disposable diaper, comprising: an absorbent pad assembly having an absorbent pad, a pair of waistline portions, a crotch portion intermediate said waistline portions, a front surface, a back surface, a pair of side edges, a pair of end edges connecting said side edges, a plurality of longitudinally extending folds defining a box-pleat configuration of the pad assembly, said pad assembly having a first pair of fold lines defining a longitudinally extending central panel, and a second pair of fold lines defining a pair of intermediate panels overlying the front surface of the central panel and a pair of outermost panels overlying the intermediate panels, said pad assembly having elastic band means extending between said outermost panels and being secured to the front surface of both of said outermost panels, and a pleated end section of the pad assembly being folded over said band means and having portions retained against the front surface of the pad assembly.

19. The diaper of claim 18 wherein the outermost panels of said end section are retained against the underlying outermost panels.

20. The diaper of claim 18 wherein the central panel of said end section is retained against the underlying central panel intermediate said second fold lines.

* * * * *